United States Patent [19]

Bock et al.

[11] 4,101,578

[45] Jul. 18, 1978

[54] CYCLOALIPHATIC TRIAMINES

[75] Inventors: Manfred Bock, Leverkusen; Josef Pedain, Cologne; Rudolf Braden, Odenthal, all of Germany

[73] Assignee: Bayer Aktiengesellschaft, Leverkusen, Germany

[21] Appl. No.: 778,632

[22] Filed: Mar. 17, 1977

[30] Foreign Application Priority Data

Apr. 2, 1976 [DE] Fed. Rep. of Germany ....... 2614244

[51] Int. Cl.$^2$ ............................................. C07C 87/02
[52] U.S. Cl. ........................... 260/563 R; 260/453 A; 260/464; 260/561 R
[58] Field of Search ..................................... 260/563 R

[56] References Cited

U.S. PATENT DOCUMENTS

| | | | |
|---|---|---|---|
| 2,534,088 | 12/1950 | Webb | 260/563 X |
| 3,584,045 | 6/1971 | Feldman et al. | 260/563 |
| 3,625,986 | 12/1971 | Feldman et al. | 260/563 X |
| 3,723,526 | 3/1973 | Edgerton | 260/563 |

*Primary Examiner*—Robert V. Hines
*Attorney, Agent, or Firm*—Gene Harsh; Lawrence S. Pope; Frederick H. Colen

[57] ABSTRACT

This invention relates to new cycloaliphatic triamines which are valuable intermediate products for synthetic resins, above all for lightfast and weather resistant polyurethane resins and in particular for solvent-free or low solvent polyurethane lacquers.

1 Claim, No Drawings

CYCLOALIPHATIC TRIAMINES

BACKGROUND OF THE INVENTION

Polyamines are already known as intermedite products for lightfast and weather resistant polyurethane lacquers, for example, hexamethylene diamine, 3-aminomethyl-3,5,5-trimethylcyclohexaylamine and 4,4'-diaminodicyclohexyl methane have achieved a position of great commercial importance as starting materials. The diisocyanates produced from these diamines, however, have serious disadvantages if used for the manufacture of two-component polyurethane lacquers. Thus, they have a low functionality of only 2, which means that two-component polyurethane lacquers would require longer curing times than are conventionally used in practice. In addition, they have the very serious disadvantage of a high vapor pressure which considerably reduces their usefulness as two-component reaction lacquers since they constitute a health hazard. In practice, this has prevented pure diisocyanates from acquiring any importance as lacquer polyisocyanates and instead reaction products of these diisocyanates still containing free isocyanate groups are used as hardener components.

Known reaction products of this kind include the reaction products of diisocyanates with polyalcohols such as trimethylolpropane. Polyisocyanates with biuret groups obtained as reaction products of diisocyanates (e.g. hexamethylene diisocyanate) with water have also achieved considerable commercial importance.

Compared with the diisocyanates mentioned above, these reaction products have important advantages as reactants in two-component polyurethane lacquers. For example, their functionality is higher than two and they have a low vapor pressure and are therefore physiologically harmless. However, the adduct formation also gives rise to disadvantages. The viscosity of these adducts is several times higher than that of the monomeric diisocyanate, the proportion of isocyanate reactive groups in the adducts is reduced to less than half and the preparation of these products requires expensive production processes such as thin layer distillation or extraction to isolate the monomeric diisocyanates.

Modern commercial application of these products is to some extent made difficult by these disadvantages. In view of the regulations for environmental protection and in order to save raw materials (solvents) and energy, the consumer of polyurethane lacquers seek as far as possible to use little or no solvent in his processes and, therefore, attaches considerable importance to low viscosity binders. For application of low solvent lacquers in conventional low pressure spray plants, a pigmented lacquer binder must have a viscosity of from 190 to 240 cP at room temperature. All physiologically harmless aliphatic polyisocyanates hitherto known have viscosities above this range and must be diluted with solvents.

There is, therefore, a demand for a polyamine capable of being converted into a polyisocyanate which does not have these disadvantages.

It was, therefore, an object of the present invention to provide polyamines having more than two amino groups in the molecule and a process for their preparation. It was required that these amines should react with phosgene to form odorless polyisocyanates which were liquid at room temperature and could be converted into physiologically harmless polyurethane lacquers.

This problem is solved by the synthesis of new cycloaliphatic triamines described below.

SUMMARY OF THE INVENTION

The invention relates to triamines of the general formula (I)

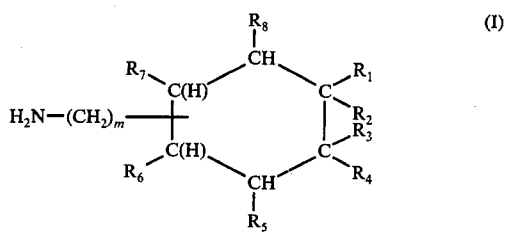

in which $R_1$, $R_2$, $R_3$ and $R_4$, which may be the same or different, represent hydrogen, a methyl group or the group $-(CH_2)_n-NH_2$ where $n$ represents an integer of from 1 to 3 and two of the groups represented by $R_1$, $R_2$, $R_3$ and $R_4$ are $-(CH_2)_n-NH_2$ groups; $m$ represents 0, 1 or 2 and $R_5$, $R_6$, $R_7$ and $R_8$ are the same or different and represent hydrogen or a methyl group, the total number of methyl groups represented by $R_5$, $R_6$, $R_7$ and $R_8$ being limited to a maximum of 2.

This invention also relates to a process for the preparation of these triamines, characterized in that compounds represented by the following formula (II)

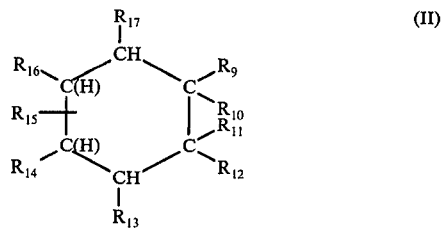

are subjected to a hydrogenation reaction in the presence of ammonia. In the above formula (II), $R_9$, $R_{10}$, $R_{11}$ and $R_{12}$ may be the same or different and represent hydrogen, a methyl group or $-(CH_2)_r-CN$ where $r$ represents 0, 1 or 2 and two of the groups represented by $R_9$, $R_{10}$, $R_{11}$ and $R_{12}$ are $-(CH_2)_r-CN$ groups; $R_{15}$ represents $-CN$, $-CH_2-CN$, $-CHO$ or $-NH_2$ and $R_{13}$, $R_{14}$, $R_{16}$, and $R_{17}$ may be the same or different and represent hydrogen or a methyl group and the total methyl groups represented by $R_{13}$, $R_{14}$, $R_{16}$ and $R_{17}$ is limited to a maximum of 2.

DETAILED DESCRIPTION OF THE INVENTION

The starting compounds II used in the process according to the invention are prepared by the reaction scheme indicated below, in which $R_9$, $R_{10}$, $R_{11}$, $R_{12}$, $R_{13}$, $R_{14}$, $R_{16}$ and $R_{17}$ have the meanings mentioned above.

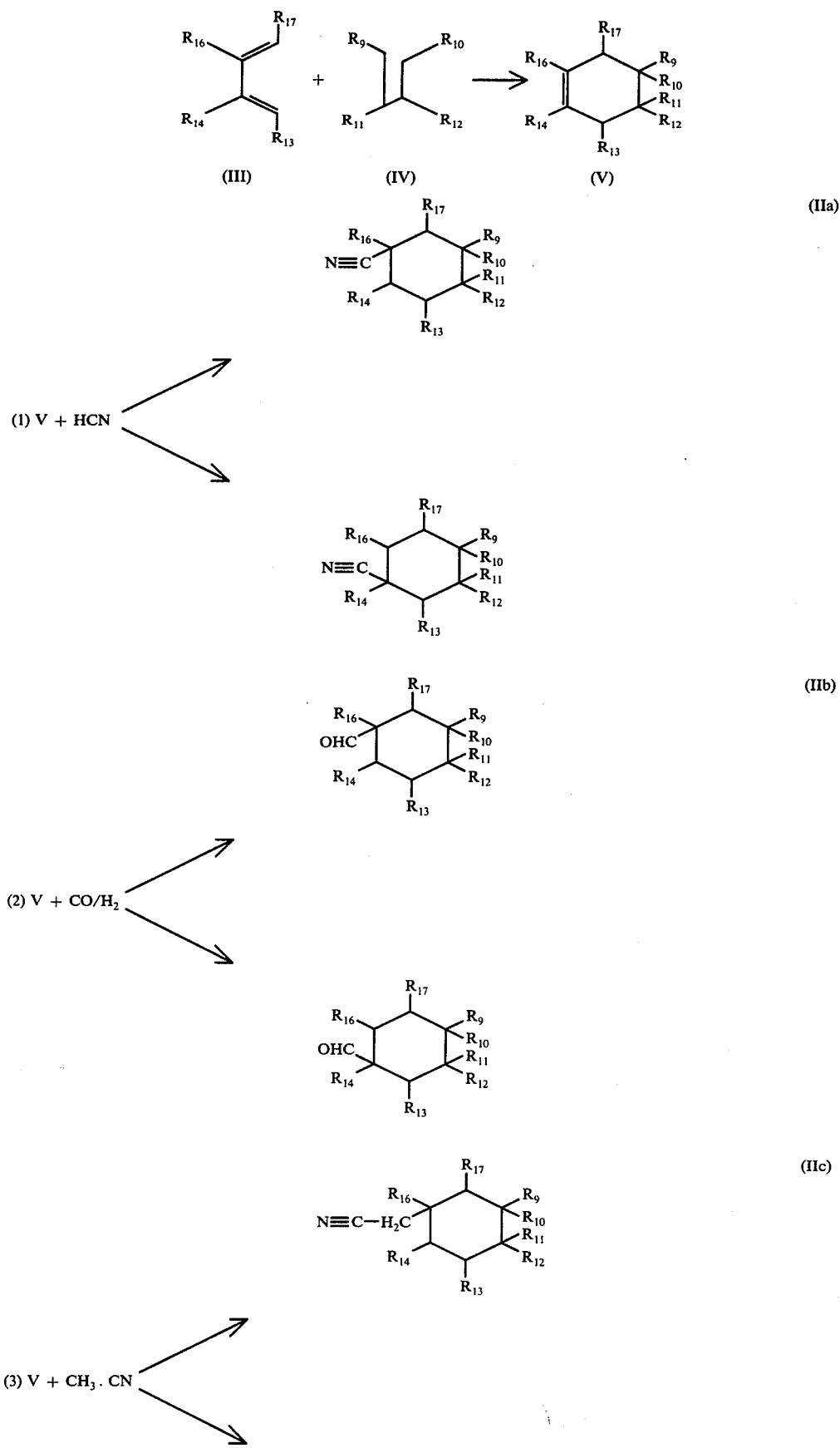

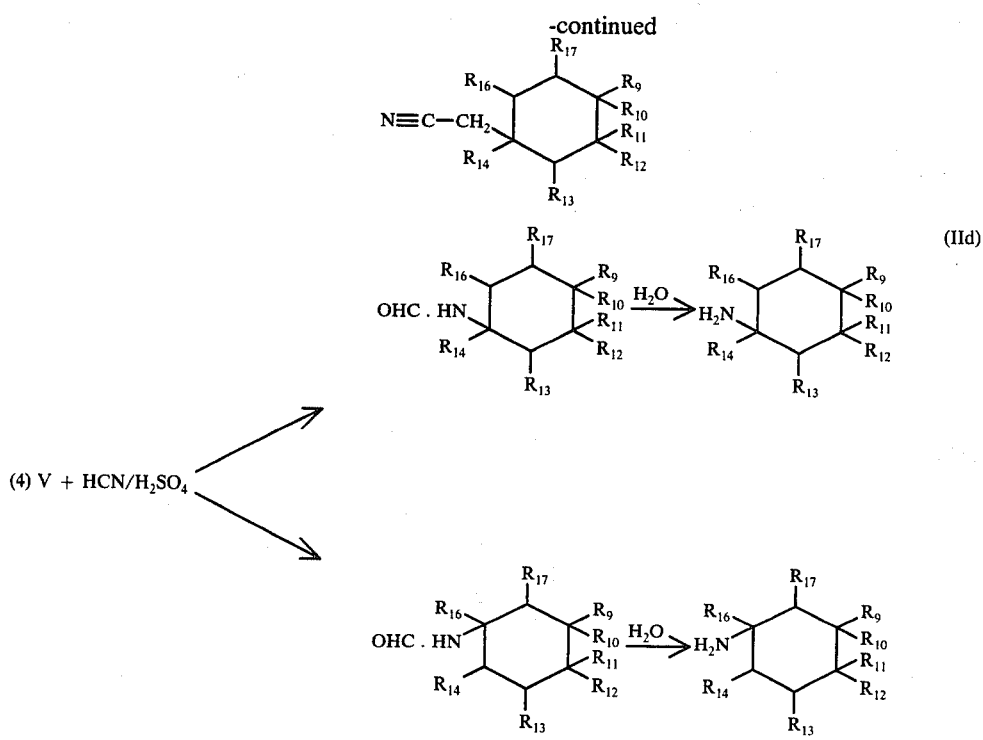

In the first reaction step, a singly unsaturated intermediate product (V) is prepared from a diene (III) and dicyanoalkene (IV) by the known Diels-Alder reaction. This reaction is preferably carried out as follows:

The diene is reacted with the dienophil at autogenous pressure in a stirrer autoclave at temperatures of between about 20° and 200° C, preferably between about 120° and 170° C. The reaction can be improved by the addition of suitable catalysts in a known manner. It may be convenient to use an inert solvent for this reaction. This solvent may subsequently be removed from the reaction mixture by distillation to isolate the Diels-Alder product or the next reaction stage may be carried out in the solvent without isolating the cyclohexene derivative.

Reaction of the intermediate product (V) with hydrocyanic acid, carbon monoxide/hydrogen, acetonitrile or sulphuric acid/hydrocyanic acid (Ritter reaction) yields the starting compounds (II) required for the process according to the invention.

Reaction of the intermediate product (V) with hydrocyanic acid gives rise to the isomeric mixture (IIa) in accordance with the above equation (1). This reaction (1) is generally carried out as follows:

The unsaturated intermediate product (V) is reacted with hydrocyanic acid, preferably twice its equivalent quantity, in an inert solvent such as tetrahydrofuran or toluene in a reactor at temperatures of between about 50° and 150° C, preferably between about 100° and 120° C, at autogenous pressure. Numerous complex compounds are suitable as catalysts, preferably complexes of the 8th subGroup of the Periodic System of Elements such as $Ni[P(OC_6H_5)_3]_4$ with zinc chloride and triphenylphosphite.

The isomeric mixtures (IIb) are obtained by reacting the intermediate product (V) with carbon monoxide/hydrogen in accordance with equation (2). This reaction is generally carried out as follows:

The aforesaid cyclohexene dinitriles are introduced into a high pressure vessel together with a solvent which is inert under the conditions of hydroformylation such as xylene, toluene, benzene, methylcyclohexane, cyclohexane, dioxane or tetrahydrofuran and a hydroformylation catalyst such as rhodium or cobalt compounds, in particular rhodium complexes, which may contain carbon monoxide, tertiary organic phosphines or phosphites and halogen atoms as ligands. Carbon monoxide and hydrogen are forced in under pressure at a ratio of between about 0.5:1 and 2:1, and the reaction is carried out at a pressure of from about 50 to 300 bar and temperatures of between about 120° and 190° C, in particular between about 140° and 180° C, over a period of less than about 6 hours. After termination of the reaction, the solvents and hydroformylation products are separated from the catalyst-containing residue by known methods such as distillation, optionally at reduced pressure. The residue with catalyst obtained after distillation can be used for subsequent reactions or roasted to recover the catalyst metal. Alternatively, hydroformylation of the cyclohexene dinitriles may be carried out continuously in a suitable apparatus.

Reaction of the intermediate product (V) with acetonitrile according to equation (3) gives rise to the mixture of isomers (IIc). This reaction is generally carried out as follows:

The olefin (V) is put under pressure at elevated temperature with a starter in acetonitrile or acetonitrile-solvent mixtures for the purpose of radical addition, the acetonitrile being present in up to about 10 times molar excess. The autogeneous pressure established in the reactor depends on the temperatures employed, which are between about 50° and 180° C. The starters used may be any conventional radical forming compounds, in particular tertiary butyl peroxide used at 145° C. The reaction may also be designed to proceed continuously.

If the intermedite product (V) is reacted with hydrocyanic acid/sulphuric acid and then subjected to hydrolysis as in (4) according to the known Ritter reaction and as described for example in German Offenlegungsschrift No. 1,965,004 which corresponds to U.S. Pat. No. 3,787,575, the isomeric mixtures (IId) are obtained. This reaction is generally carried out as follows:

The intermediate product (V) is introduced dropwise into a dilute aqueous sulphuric acid of about 50 to 96%, preferably about 60 to 70%, to which an excess of hydrocyanic acid has been added. After prolonged heating with reflux of the hydrocyanic acid, the reaction mixture is taken up in water and adjusted to about pH 4. This causes separation of the formamido compound (see equation 4) which is subsequently hydrolyzed in a weakly acid aqueous medium to the isomeric mixture (IId).

For this reaction, it is particularly suitable to use those intermediate products (V) in which the —C═C— double bond is marked by a methyl substituent ($R_{14}$ or $R_{16}$ is —$CH_3$).

The following compounds may be used as diene component (III) for preparation of the intermediate compound (V): Butadiene, 1-methylbutadiene, 2-methylbutadiene and 2,3-dimethylbutadiene.

The following dicyanoalkenes, for example, may be used as dienophilic reactants: Maleic acid dinitrile; 2,3-diemthyl-maleic acid dinitrile; fumaric acid dinitrile; glutaconic acid dinitrile; α-methylene-glutaric acid dinitrile; α-methyl-glutaconic acid dinitrile; β-methyleneglutaric acid dinitrile; β-methyl-glutaconic acid dinitrile; 2-ethylidene-glutaric acid dinitrile; 2-isopropylideneglutaric acid dinitrile; dicrotonic acid dinitrile; 1,4-dicyanobutene-2 and 1,4-dicyanobutene-1.

From such dicyanoalkenes and the above mentioned dienes are formed the intermediate compounds (V) which are converted into the intermediate products (IIa to IId) required for the process according to the invention. The following are examples of these products (IIa - IId); they are in all cases present as stereoisomeric mixtures:

1,4 (or 1,5)-dicyano-2-(2-cyanoethyl)-cyclohexane;
1-cyano-2-(2-cyanoethyl)-4(or 5)-formyl-cyclohexane;
1-cyano-2-(2-cyanoethyl)-4(or 5)-cyanomethylcyclohexane;
1-cyano-2-(2-cyanoethyl)-4(or 5)-methyl-4(or 5)-cyanocyclohexane;
1-cyano-2-(2-cyanoethyl)-4-(or 5)-methyl-4(or 5)-formylcyclohexane;
1-cyano-2-(2-cyanoethyl)-4(or 5)-methyl-4(or 5)-cyanomethylcyclohexane;
1-methyl-3(or 4)-cyano-3-(or 4)-(2-cyanoethyl)-cyclohexylamine;
1,3(or 1,4)-dicyano-1-(2-cyanoethyl)-cyclohexane;
1-cyano-1-(2-cyanoethyl)-3(or 4)-formyl-cyclohexane;
1-cyano-1-(2-cyanoethyl)-3(or 4)-cyanomethylcyclohexane;
1-cyano-1-(2-cyanoethyl)-3(or 4)-methyl-3(or 4)-cyanocyclohexane;
1-cyano-1-(2-cyanoethyl)-3(or 4)-methyl-3(or 4)-formylcyclohexane;
1-cyano-1-(2-cyanoethyl)-3(or 4)-methyl-3(or 4)-cyanomethyl-cyclohexane;
1,2-di-cyanomethyl-4-(or 5)-cyano-cyclohexane;
1,2-di-cyanomethyl-4-(or 5)-formyl-cyclohexane;
1,2,4(or 1,2,5)-tris-cyanomethyl-cyclohexane;
1,2-di-cyanomethyl-3(or 6)-methyl-4(or 5)-cyanocyclohexane;
1,2-di-cyanomethyl-3-(or 6)-methyl-4-(or 5)-formylcyclohexane and
1,2,4(or 1,2,5)-tris-cyanomethyl-3-(or 6)-methylcyclohexane.

In the process according to the invention, the starting compounds II (IIa, IIb, IIc or IId) mentioned by way of example are catalytically hydrogenated in the presence of ammonia, whereby the nitrile groups present are reduced to the corresponding aminomethyl groups. At the same time, any formyl groups present are reductively aminated to the corresponding aminomethyl groups. Catalytic hydrogenation of the nitrile groups and reductive amination of the aldehyde function, if any, are carried out simultaneously. The reduction is carried out in the presence of about 2 to 30 mol of ammonia per mol of compound (II), in particular about 3 to 15 mol of ammonia per mol of (II), at a temperature of about 30° to 180° C and hydrogen pressure of about 5 to 200 bar, in particular at about 60° to 150° C and about 30 to 150 bar. The catalysts used for reduction are preferably metals of atomic numbers 23 to 30 and 42 to 46, for example catalysts containing nickel and/or cobalt such as Raney nickel and/or Raney cobalt.

According to one preferred method of carrying out the process, Raney cobalt or cobalt catalysts with acidic carriers such as silicic acid are used. In one embodiment of the process according to the invention, catalytic reductive amination of the formyl group with simultaneous hydrogenation of the nitrile groups is carried out in the presence of catalytic quantities of acids or ammonium salts such as acetic acid, propionic acid, trifluoroacetic acid, ammonium chloride or ammonium phosphate. The hydrogenation reaction may be carried out in a solvent. Suitable solvents include alcohols such as i.e. methanol, ethanol, isopropanol, cyclohexanol, ethyleneglycol or ethyleneglycolmonomethylether, ethers such as i.e. ethyleneglycoldimethylether or diethylether, cyclic ethers such as tetrahydrofuran and dioxane, hydrocarbons such as cyclohexane, benzene, toluene, xylene and water. It may be advantageous to use a solvent mixture. When formylnitrile is produced by hydroformylation, the solvent used for hydroformylation may also be used for hydrogenation. The preferred solvents are tetrahydrofuran and toluene. It is a particular advantage of the process that catalytic reduction can be carried out in the same solvent as that in which the nitrile compound was prepared.

This reduction or reductive amination gives rise to the products (I) according to the invention. Particularly preferred representatives of the products according to the invention include, for example, the isomeric mixtures obtainable from the cyano compounds (II) mentioned above, for example the isomeric mixture of 1,4-bis-(aminomethyl)-2-(3-aminopropyl)-cyclohexane and 1,3-bis-(aminomethyl)4-(3-aminopropyl)-cyclohexane (VI)

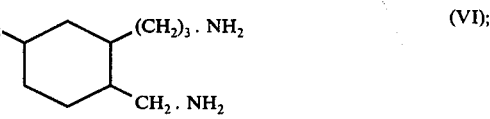

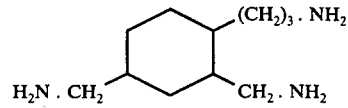

the isomeric mixture of 1,4-bis-(aminomethyl)-1-(3-aminopropyl)-cyclohexane and 1,3-bis-(aminomethyl)-1-(3-aminopropyl)-cyclohexane (VII)

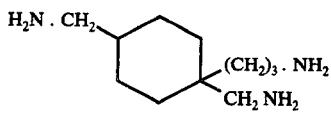

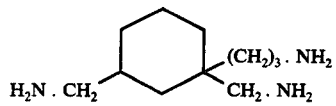

(VII);

the isomeric mixture of 1-aminomethyl-2-(3-aminopropyl)-4-(2-aminoethyl)-cyclohexane and 1-aminomethyl-2-(3-aminopropyl)-5-(2-aminoethyl)-cyclohexane (VIII)

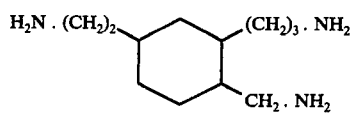

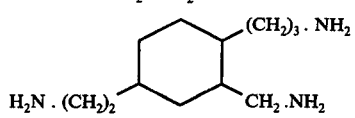

(VIII);

the isomeric mixture of 1-amqnomethyl-1-(3-aminopropyl)-4-(2-aminoethyl)-cyclohexane and 1-aminomethyl-1-(3-aminopropyl)-3-(2-aminoethyl)-cyclohexane (IX)

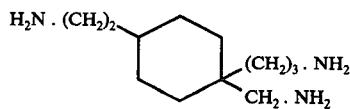

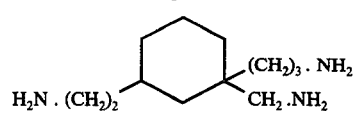

(IX);

the isomeric mixture of 1-methyl-3-(3-aminopropyl)-4-aminomethyl-cyclohexylamine and 1-methyl-3-aminomethyl-4-(3-aminopropyl)-cyclohexylamine (X)

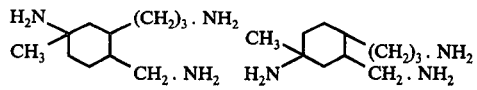

(X);

and the isomeric mixture of 1-methyl-4-aminomethyl-4-(3-aminopropyl)-cyclohexylamine and 1-methyl-3-aminomethyl-3-(3-aminopropyl)-cyclohexylamine (XI)

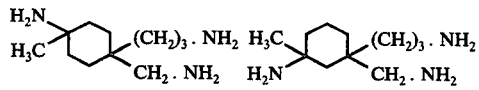

(XI).

The polyamines according to the invention are water-clear liquids at about 20° C which can be reacted with phosgene in a solvent to yield polyisocyanates which in turn can be worked up into two-component polyurethane lacquers.

The polyisocyanates obtained from the polyamines according to the invention are completely odorless and have an advantageous, very low viscosity.

In addition, the polyamines according to the invention also serve as intermediate products for other synthetic resins; for example they can be used successfully as hardeners for epoxide resins. They are also suitable for use as corrosion preventing additives for liquid propellants and fuels.

EXAMPLES

Example 1

1-Aminomethyl-2-(3-aminopropyl)-4-(or 5)-aminomethyl-cyclohexane

A. Stage 1: 1-Cyano-2-(2-cyanoethyl)-4-(or 5)-formyl-cyclohexane 300 g (1.88 mol) of 1-cyano-2-(2-cyanoethyl)-cyclohexene-4 are dissolved in 600 ml of toluene and hydroformylated with carbon monoxide/hydrogen (molar ratio 1: 1) in a refined steel stirrer autoclave at 170° C and 200 to 250 bar over a period of 4 hours in the presence of 0.05% of $[(C_6H_5)_3P]_3RhCl_3$. After removal of the solvent, the reaction product is distilled in a high vacuum. 1-Cyano-2-(2-cyanoethyl)-4-(or 5)-formyl-cyclohexane which has a boiling point of 178° C/0.18 Torr is obtained as a colorless, viscous liquid in a yield of 267 g (75%). $n_D^{25}$: 1.5014

Analysis: (Figures here and subsequently in all cases in percentages by weight): Found: C 69.3, H 7.5, N 14.6, O 8.9; Theory: C 69.4, H 7.3, N 14.7, O 8.4.

B. Stage 1: 1-Cyano-2-(2-cyanoethyl)-4-(or 5)-cyanocylochexane 160 g (1 mol) of 1-cyano-2-(2-cyanoethyl)-cyclohexene-4 are introduced into a reactor together with 4 g of zinc chloride, 20 g of $Ni[P(OC_6H_5)_3]_4$, an excess of triphenylphosphite and 80 ml of hydrocyanic acid in 400 ml of tetrahydrofuran and reacted for 3 hours at 120° C. After removal of the catalyst and evaporation of the solvent, 1-cyano-2-(2-cyanoethyl)-4-(or 5)-cyanocyclohexane is obtained as a colorless liquid in a yield of 97 g (52%) by high vacuum distillation at 169° C/0.18 Torr.

$n_D^{25}$: 1.5105

Analysis: Found: C 70.4, H 6.8, N 22.4; Theory: C 70.5, H 6.9, N 22.4.

$C_1$. Stage 2: Hydrogenation of the formylation product 200 g (1.05 mol) of 1-cyano-2-(2-cyanoethyl)-4-(or 5)-formyl-cyclohexane are hydrogenated in 400 ml of tetrahydrofuran in the presence of 50 g of Raney cobalt catalyst, 300 ml of liquid ammonia and 3 to 4 ml of glacial acetic acid at a temperature of 120° to 150° C and hydrogen pressure of 120 to 150 bar in the course of 4 hours. The catalyst is then removed and the reaction solution distilled. 1-Aminomethyl-2-(3-aminopropyl)-4-(or 5)-aminomethyl-cyclohexane boils at 129° C/0.13 Torr and is obtained as a colorless liquid in a yield of 144 g (69%).

$n_D^{25}$: 1.5088

Analysis: Found: C 66.2, H 12.4, N 20.9; Theory: C 66.3, H 12.5, N 21.1.

$C_2$. Stage 2: Hydrogenation of the cyanic acid adduct 100 g (0.53 mol) of 1-cyano-2-(2-cyanoethyl)-4-(or 5)-cyanocylochexane are hydrogenated in 500 ml of tetrahydrofuran for 3 hours at 120° to 130° C and a hydrogen pressure of 100 to 120 bar in the presence of 100 g of ammonia and 10 g of Raney cobalt catalyst. After removal of the catalyst and distillation in a high vacuum, 1-aminomethyl-2-(3-aminopropyl)-4-(or 5)-aminomethyl-cyclohexane is isolated in a yield of 84 g (79%). This product is identical in its properties to the amine obtained from 1-cyano-2-(2-cyanoethyl)-4(or 5)-formyl-cyclohexane (Example 1, C₁-Stage 2).

Example 2

1-Aminomethyl-1-(3-aminopropyl)-3(or 4)-aminomethyl-cyclohexane

Stage 1: 1-Cyano-1-(2-cyanoethyl)-3(or 4)-formyl-cyclohexane 300 g (1.88 mol) of 1-cyano-1-(2-cyanoethyl)-cyclohexene-3 are hydroformylated in 600 ml of toluene by the method described in Example 1 A. 1-Cyano-1-(2-cyanoethyl)-3(or 4)-formyl-cyclohexane which has a boiling point of 166°–168° C at 0.15 Torr is obtained from the reaction mixture as a colorless, viscous liquid in a yield of 310 g (87%).

$n_D^{25}$: 1.4962

Analysis: Found: C 69.2, H 7.8, N 14.7, O 9.1; Theory: C 69.4, H 7.3 N 14.7, O 8.4.

Stage 2: Hydrogenation of the formyl product 200 g (1.05 mol) of 1-cyano-1-(2-cyanoethyl)-3(or 4)-formyl-cyclohexane are hydrogenated in 400 ml of dioxane in the presence of catalyst, liquid ammonia and glacial acetic acid by the method indicated in Example 1 (C₁-Stage 2).

The reaction mixture is worked up in the usual manner. 1-Aminomethyl-1-(3-aminopropyl)-3(or 4)-amimomethyl-cyclohexane boiling at 115° to 117° C/0.09 Torr is obtained as colorless liquid in a yield of 150 g (72%).

$n_D^{25}$: 1.5076

Analysis: Found: C 66.3, H 12.6, N 21.2; Theory: C 66.3, H 12.5, N 21.1.

Example 3

1-Aminomethyl-1-(3-aminopropyl)-3(or 4)-amino-3(or 4)-methyl-cyclohexane

Stage 1: 1-Cyano-1-(2-cyanoethyl)-3(or 4)-amino-3(or 4)-methyl-cyclohexane 174 g (1.0 mol) of 1-cyano-1-(2-cyanoethyl)-3(or 4)-methyl-cyclohexene-3- are introduced into 270 g of 80% sulphuric acid and 300 ml of cyanic acid. The reaction mixture is then heated for 4 hours with mild reflux of the hydrocyanic acid. Excess cyanic acid is subsequently distilled off. The reaction mixture is taken up in 900 ml of water and adjusted to pH 4 and 1-cyano-1-(2-cyanoethyl)-3(or 4)-methyl-3(or 4)-formamide-cyclohexane is isolated from it. The product is hydrolyzed in dilute hydrochloric acid at 50° C. 1-Cyano-1-(2-cyanoethyl)-3(or 4)-amino-3(or 4)-methyl-cyclohexane is extracted from the alkaline medium with toluene and distilled at 138° C/0.14 Torr. Yield: 92 g (48%).

$n_D^{25}$: 1.5434

Analysis: Found: C 69.2, H 8.9, N 21.5; Theory: C 69.1, H 8.9, N 21.9.

Stage 2: Hydrogenation of the aminonitrile 160 g (0.84 mol) of 1-cyano-1-(2-cyanoethyl)-3(or 4)-amino-3(or 4)-methyl-cyclohexane are taken up in 500 ml of methanol and hydrogenated for 5 hours at 90° C/120–150 bar hydrogen in the presence of 100 g of liquid ammonia and 30 g of Raney cobalt catalyst. After removal of the catalyst, 1-aminomethyl-1-(3-aminopropyl)-3(or 4)-amino-3(or 4)-methyl-cyclohexane is distilled in a high vacuum. Bp: 125°–128° C/0.18 Torr. Yield: 123 g (74%).

$n_D^{25}$: 1.4936

Analysis: Found: C 66.2, H 12.4, N 20.9, Theory: C 66.3, H 12.5, N 21.1.

Example 4

This Example demonstrates the possibility of preparing a triisocyanate, in this case 1-isocyanatomethyl-1-(3-isocyanatopropyl)-3(or 4)-isocyanatomethyl-cyclohexane.

150 g (0.75 mol) of 1-aminomethyl-1-(3-aminopropyl)-3(or 4)-aminomethyl-cyclohexane are dissolved in 1.5 liters of chlorobenzene in a three-necked flask and reacted with CO₂ at the boiling point of the solvent until the reaction is complete. The temperature is lowered to −5° C for phosgenation. About 180 g (1.8 mol) of phosgene are condensed in the cold suspension. The reaction mixture is then slowly heated until the solvent boils while additonal phosgene is continuously added. The phosgenation is continued until a clear solution is obtained. This solution is then freed from excess phosgene by washing with nitrogen and subsequently concentrated by evaporation under vacuum. 1-isocyanatomethyl-1-(3-isocyanatopropyl-3(or 4)-isocyanatomethyl-cyclohexane boiling at 166°–168° C/0.2 Torr is obtained by high vacuum distillation as a pale, yellowish liquid in a yield of 157 g (75%).

$n_D^{25}$: 1.5142 Viscosity: 70 cP (20° C).

Analysis: Found: C 60.5, H 6.9, N 14.9, O 16.8; Theory: C 60.6, H 6.9, N 15.2, O 17.3.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Triamines of the formula (I)

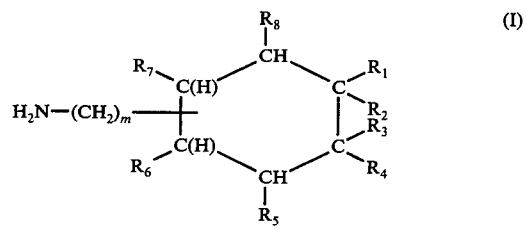

in which $R_1$, $R_2$, $R_3$ and $R_4$ are the same or different and represent hydrogen, a methyl group or the group —(CH₂)ₙ—NH₂ where $n$ represents an integer of from 1 to 3 and two of the groups represented by $R_1$, $R_2$, $R_3$ and $R_4$ are —(CH₂)ₙ—NH₂ groups; $m$ represents 0, 1 or 2; and $R_5$, $R_6$, $R_7$ and $R_8$ are the same or different and represent hydrogen or a methyl group, the total number of methyl groups represented by $R_5$, $R_6$, $R_7$ and $R_8$ being limited to a maximum of 2.

* * * * *